(12) United States Patent
Passmore et al.

(10) Patent No.: US 6,841,161 B1
(45) Date of Patent: Jan. 11, 2005

(54) TOPICAL COMPOSITIONS

(75) Inventors: Clare Passmore, Belfast (GB); Claire Gilligan, Belfast (GB)

(73) Assignee: Galen (Chemicals) Limited, Dublin (IE)

( * ) Notice: Subject to any disclaimer, the term of this patent is extended or adjusted under 35 U.S.C. 154(b) by 0 days.

(21) Appl. No.: 09/423,715

(22) PCT Filed: May 14, 1998

(86) PCT No.: PCT/IE98/00036

§ 371 (c)(1),
(2), (4) Date: Jan. 12, 2000

(87) PCT Pub. No.: WO98/51283

PCT Pub. Date: Nov. 19, 1998

(30) Foreign Application Priority Data

May 14, 1997 (IE) .............................. S970346

(51) Int. Cl.$^7$ ........................... A61K 9/00; A01N 25/00
(52) U.S. Cl. ..................... 424/400; 424/405; 514/887; 514/937
(58) Field of Search ................................ 424/400, 405; 514/887, 937

(56) References Cited

U.S. PATENT DOCUMENTS

| | | | | |
|---|---|---|---|---|
| 5,206,021 A | | 4/1993 | Dookhith | 424/405 |
| 5,525,597 A | * | 6/1996 | Hainrihar et al. | 514/75 |
| 5,658,583 A | | 8/1997 | Zhang et al. | 424/402 |
| 5,854,246 A | * | 12/1998 | Francois et al. | 514/252 |
| 2002/0131983 A1 | * | 9/2002 | Becker et al. | 424/234.1 |

FOREIGN PATENT DOCUMENTS

| | | | | |
|---|---|---|---|---|
| WO | 9104733 | | 4/1991 | |
| WO | WO 9108670 A1 | * | 6/1991 | A01N/65/00 |

OTHER PUBLICATIONS

Database USPATFULL on STN, US 5525597 (Hainrihar et al.), abstract, Jun. 1996.*
Database CAPLUS on STN, WO 9108670–A1 (Guerrini), abstract, Jun. 1991.*
The Condensed Chemical Dictionary, 10$^{th}$ Ed., Gessner G. Hawley, Van Nostrand Reinholg Co., New York (1981), pp. 252, 602 and 603.*
Merriam–Webster's Collegiate Dictionary, 10$^{th}$ Ed., Merriam–Webster, Inc., Springfield, MA (1998) p. 355.*
*Drug release studies on oil–water emulsion based on a eutectic mixture of lidocaine and prilocaine as the dispersed phase,* Nyquist–Mayer et al., Journal of Pharmaceutical Sciences, vol. 75, No. 4, Apr. 1996, pp. 365–373.

* cited by examiner

*Primary Examiner*—Sreeni Padmanabhan
*Assistant Examiner*—Lauren Q. Wells
(74) *Attorney, Agent, or Firm*—Jay H. Maioli (57) ABSTRACT

The invention concerns a topical composition comprising an emulsion of at least one discontinuous phase in a continuous phase, the or each discontinuous phase including a eutectic mixture of first and second pharmaceutically acceptable components which are both pharmacologically active agents and the continuous phase being provided by a pharmaceutically acceptable carrier, the eutectic mixture having a melting point below 40° C. The topical composition may additionally comprise, in the eutectic mixture, a third or fourth pharmaceutically acceptable component.

29 Claims, 9 Drawing Sheets

TOPICAL COMPOSITIONS

This Application is a national stage entry of PCT/IE98/00036.

This invention relates to topical compositions for administration to the human or animal species, the compositions containing a eutectic mixture of pharmacologically active agents which exhibit enhanced mutual topical absorption. As used herein, the term 'topical compositions' is intended to mean compositions for administration to any accessible body surface such as, for example, the skin and mucosal epithelia such as nasal, rectal, buccal, ocular, pulmonary and rectal epithelia, as well as, the gastrointestinal epithelium.

A eutectic mixture of two eutectic-forming solids shows, upon intimate admixture of the two solids, a homogeneous liquid phase above the melting point of the higher melting component. Usually, although not always, the required intimate mixture involves melting the two eutectic-forming solids together. A plot of melting point versus relative composition of the two eutectic-forming solids displays a minimum point between two intersecting lines at which a homogeneous liquid phase coexists with each of the respective homogeneous solid phases. This point is known as the eutectic point or eutectic temperature.

Most published scientific literature concerning the formation of eutectic mixtures relates to the field of metallurgy, in particular to the formation of solders and the behaviour of alloys (Jacobsen, D. M. and Humpston, G. 1995. "Depressing the melting point of solders and brazes by eutectic alloying." GEC Journal of Research Vol. 12. p. 112), where the formation of lower melting point eutectic mixtures is generally regarded as advantageous. By contrast, however, the formation of a eutectic mixture in the pharmaceutical or veterinary fields in which a liquid phase develops at normal storage temperatures, is often regarded as problematic and undesirable. Thus, in the textbook "Pharmaceutical Dosage Forms and Drug Delivery Systems", 6th edition 1995 (Ansel, H. C., Popovich, N. G. and Allen, L. V. Jr. page 172. Williams and Wilkins, USA), it is taught that eutectic formation in common pharmaceutical dosage forms is undesirable and can be prevented, for example, by the use of an inert diluent e.g. lactose in sufficient quantity to prevent intimate contact between the eutectic-forming solid components. U.S. Pat. No. 5,512,300 also teaches that formation of eutectic mixtures results in stability problems in solid dosage forms and is, therefore, to be avoided. U.S. Pat. No. 5,512,300 further teaches a method of preventing formation of such mixtures by alkali metal treatment.

Transdermal delivery of a pharmacologically active agent (drug) conventionally requires that the drug be presented to the absorption barrier—the skin—in a lipophilic form in solution. In addition, drug levels in solution should be as close as possible to saturation, to provide the highest possible concentration gradient across the absorption barrier.

Conventionally, a solution of a drug in a lipophilic form is achieved by including either a water miscible co-solvent or an emulsified oil phase in which the drug is first dissolved in an oil or mixture of oils as solvent. However, whilst both of these measures hinder drug penetration by providing a competing phase for drug migration, the negative effect of the latter measure is more pronounced. In addition, the use of co-solvents such as ethanol or propylene glycol are known to cause adverse local reactions on the skin and epithelia.

As a consequence of the perceived pharmaceutical formulation problems caused by eutectic mixtures, there has been only one commercial application of a eutectic mixture, specifically, a binary mixture of local anaesthetic agents, which is disclosed in EP-A-2425. Since this disclosure which was published in 1979, there have been no further commercial developments in this area.

EP-A-2425 teaches that certain mixtures of two local anaesthetics, preferably lidocaine and prilocaine, each in free base form, results in the formation of a eutectic mixture as an oil with a melting point below 40° C. EP-A-2425 exemplifies various binary eutectic mixtures of local anaesthetically active agents. EP-A-2425 does not exemplify a topical emulsion composition in which the discontinuous phase includes a eutectic mixture.

All local anaesthetically active agents possess a common structural pattern, in which a substituted aromatic hydrophobic component is linked via an amide, ester, ketone or ether group to an intermediate alkyl chain terminating in a hydrophilic moiety (Buchi, J. and Perlia, X. 1971. "Structure-activity relations and physicochemical properties of local anaesthetics." In: Lechat, P. (ed.) Local Anaesthetics, Vol 1. International encyclopaedia of pharmacology and therapeutics, Section 8. Pergamon Press, Oxford, pp. 39–130.). There is no suggestion in EP-A-2425 that pharmaceutically useful eutectic mixtures can be formed from anything other than structurally similar active agents.

Surprisingly, it has now been found that pharmaceutically useful topical compositions can be formed by incorporating, in a suitable delivery system, a eutectic mixture of at least two pharmacologically active agents, which may be structurally and/or pharmacologically diverse. These compositions achieve enhanced topical permeation for each of the pharmacologically active agents by means of improved drug release from the topical composition itself and not by interaction with the skin. Preferred compositions are those in which the agents possess complementary but different pharmacological activities.

Formulations containing more than one active drug usually present additional formulation problems due to the increased possibility of adverse physical and/or chemical interactions between the active drugs. Thus, in the standard text on dosage form design (Ansel, H. C., Popovich, N. G., Allen, L. V. *Pharmaceutical Dosage Forms and Drug Delivery Systems, 6th edition*, Williams and Williams, USA, 1995, pp. 99–154), it is stated that the drug (singular) and pharmaceutical materials must be compatible with each other. Further, the teaching in this textbook relates entirely to a formulation containing a single active drug and nowhere is it taught that a second active drug may be advantageously added to a given formulation in order to produce a beneficial effect.

The present invention surprisingly overcomes the problems referred to hereinbefore, which hinder topical drug absorption, by providing a topical composition comprising a eutectic mixture of at least two pharmaceutically acceptable components which are both pharmacologically active agents in their lipophilic (substantially water-insoluble) form, the eutectic mixture being dispersed in, but not substantially dissolved in, a hydrophilic, pharmaceutically acceptable carrier.

Accordingly, the invention provides a topical composition comprising an emulsion of at least one discontinuous phase in a continuous phase, the or each discontinuous phase including a eutectic mixture of first and second pharmaceutically acceptable components which are both pharmacologically active agents and the continuous phase being provided by a pharmaceutically acceptable carrier, the eutectic mixture having a melting point below 40° C. Preferably, the first pharmacologically active agent has a melting point between 35 and 75° C., preferably 40–50° C., and the second pharmacologically active agent has a melting point between −40 and 150° C., preferably between −5 and 90° C.

Advantageously, the topical composition additionally includes, in the eutectic mixture, a third pharmaceutically acceptable component. Preferably, the third pharmaceutically acceptable component should have a melting point between 40 and 150° C., preferably between 40 and 75° C. More preferably, the third component comprises a third pharmacologically active agent.

More advantageously, the topical composition additionally includes, in the eutectic mixture, a fourth pharmaceutically acceptable component. The fourth pharmaceutically acceptable component should have a melting point between 40 and 150° C., preferably between 40 and 75° C. More preferably, the fourth component comprises a fourth pharmacologically active agent.

More preferably, such topical compositions should contain no co-solvent or additional oil phase, so that the eutectic mixture substantially, preferably essentially, comprises the or each discontinuous phase of the emulsion.

As used herein, the term 'pharmacological agent' means any agent used in the prophylaxis or therapy of any condition affecting the health of the human or animal species. Exemplary agents useful in the invention include, but are not limited to, antimicrobial agents such as mupirocin, triclosan, chlorocresol, chlorbutol, iodine, clindamycin and econazole, anti-inflammatory analgesic compounds such as ibuprofen and ketoprofen, opioid analgesics such as fentanyl, rubefacients such as methyl nicotinate, anti-motion sickness agents such as scopolamine, antispasmodic agents such as oxybutynin, anti-worm agents such as levamisole, as well as vitamins, minerals and other nutrients.

Preferably, the first pharmacologically active agent is selected from triclosan, chlorocresol, chlorbutanol, methyl nicotinate, triprolidine, promethazine, trimeprazine, sulfiram, oxybutynin, capsaicin, testosterone enanthate or choline salicylate.

Preferably, the second pharmacologically active agent is selected from triclosan; chlorocresol, capsaicin, trimeprazine, choline salicylate, methyl nicotinate; non-steroid anti-inflammatory agents selected from arylpropionic acid derivatives such as ibuprofen, ketoprofen, fenoprofen and flurbiprofen; aryl acetic acid derivatives such as etodolac; and arylcarboxylic acids; narcotic analgesics such as fentanyl; anti-fungal agents such as econazole and ketoconazole; antibacterial agents such as mupirocin, chlorbutanol, clindamycin and iodine; anticholinergics such as oxybutynin; anthelmintics such as tetramisole; antihistaminics such as triprolidine and promethazine and antihypertensives such as propranolol.

Preferably, the third and fourth pharmacologically active agents are each selected from triclosan; chlorocresol; capsaicin, trimeprazine, choline salicylate, methyl nicotinate; non-steroid anti-inflammatory agents selected from arylpropionic acid derivatives such as ibuprofen, ketoprofen, fenoprofen and flurbiprofen; aryl acetic acid derivatives such as etodolac; and arylcarboxylic acids; narcotic analgesics such as fentanyl; anti-fungal agents such as econazole and ketoconazole; antibacterial agents such as mupirocin, chlorbutanol, clindamycin and iodine; anticholinergics such as oxybutynin; antihypertensives such as propranolol; antihistaminics such as triprolidine and promethazine; and anthelmintics such as tetramisole.

The pharmaceutically acceptable component may also be an agent not intended for use in the prophylaxis or therapy of any condition affecting the health of the human or animal species and includes, but is not limited to, lauric acid, stearyl alcohol, menthol, thymol, cinnamic acid or an ester thereof.

The pharmaceutically acceptable carrier according to this invention should be suitable for administration of the eutectic mixture; should not adversely interfere with the formation and stability of said mixture; and should be suitable for topical application. Suitable topical compositions include gels, lotions, suspensions, creams, aerosol sprays, transdermal patches, medicated dressings and soft gelatin capsules for rapid gastrointestinal absorption. Preferably, the pharmaceutical carrier of use in the invention should be substantially hydrophilic, said carrier containing substantially, preferably essentially, water as the continuous phase and there should be no lipophilic phase present, other than that formed by the eutectic mixture of the composition of the invention.

Most preferably, the pharmaceutically acceptable carrier should contain at least one gelling or suspension agent known in the art. Exemplars of suitable gelling or suspension agents include carbomers, modified cellulose derivatives, naturally-occurring, synthetic or semi-synthetic gums such as xanthan gum, acacia and tragacanth, modified starches, co-polymers such as those formed between maleic anhydride and methyl vinyl ether, colloidal silica and methacrylate derivatives sold under the trade name Eudragit™ or a mixture thereof.

Advantageously, the pharmaceutically acceptable carrier should include at least one surfactant (emulsifying agent) compatible with any pharmacologically active agents or pharmaceutically acceptable components present. Non-ionic, cationic and anionic surfactants are suitable. Non-ionic surfactants, for example, Tweens and Spans (Trade Marks) are preferred.

The topical compositions of the invention may be prepared, as an emulsion, by incorporating the eutectic mixture, for example, the binary, ternary or quaternary eutectic mixture, into the pharmaceutically acceptable carrier such that, preferably,
1. the eutectic mixture substantially, preferably essentially, comprises the oil phase at normal storage temperatures;
2. the eutectic mixture is homogeneously distributed throughout the carrier; and
3. homogeneity is maintained over normal storage periods at ambient temperature. Homogeneous distribution of the eutectic mixture may be achieved by any suitable method known in the art, such as the formation of oil-in-water emulsions, followed by the incorporation of one or more suitable viscosity builders.

The invention will now be exemplified by reference to the following Examples A–I in which various eutectic mixtures of pharmacologically active agents are identified. The invention will be further exemplified by reference to Examples 1–6 of topical compositions of the invention that show mutually enhanced drug permeation through a model hydrophobic barrier. In these examples, the mutually enhanced drug permeation occurs as a result of the composition itself and is not due to eutectic mixture-skin lipid interactions, since the penetration barrier used in Examples 1–6 is a synthetic hydrophobic polymer.

EXAMPLE A

Ibuprofen-Methyl Nicotinate Eutectic Mixture

Figure 1:
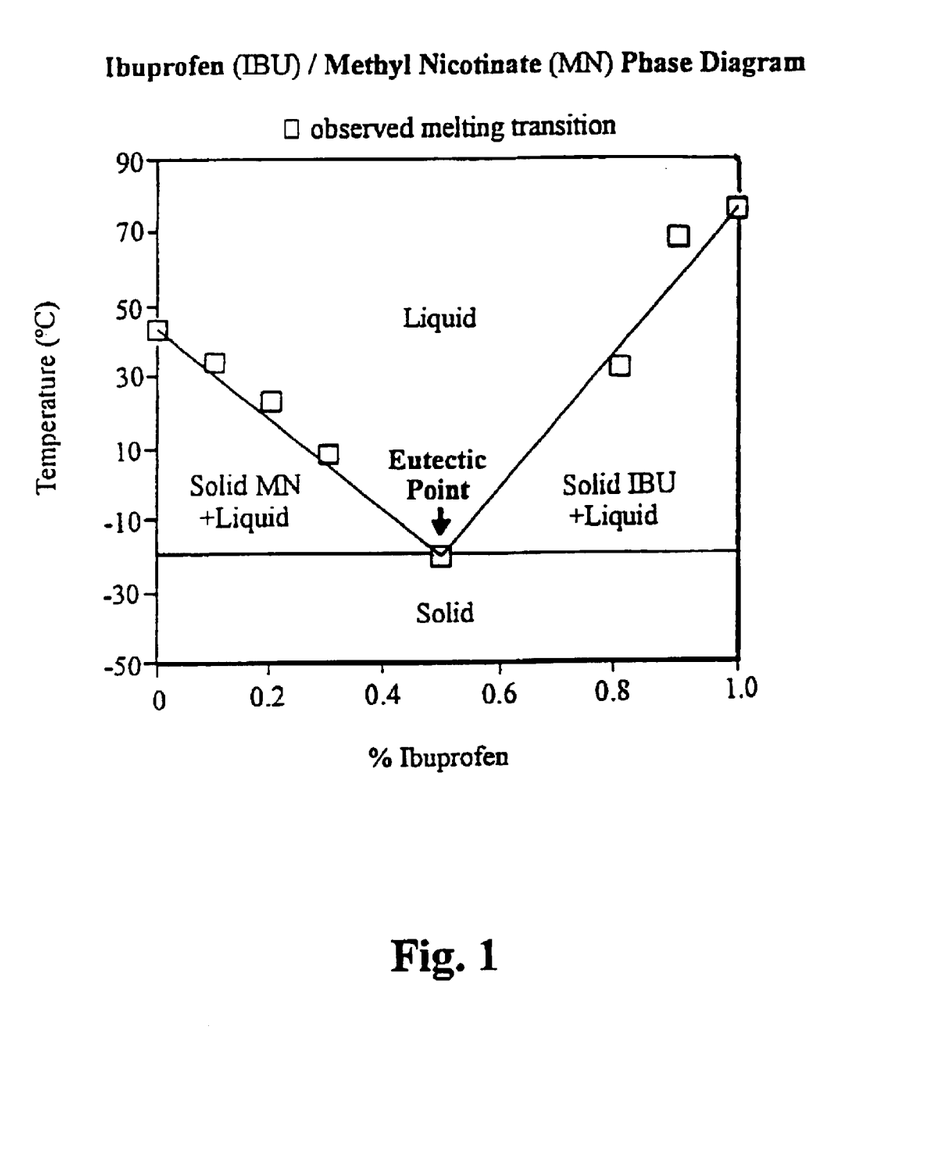

FIG. 1 is a phase diagram for the ibuprofen-methyl nicotinate system. It was prepared by determining the melting points, using differential scanning calorimetry (DSC), of systems containing from 0 to 100% by weight of methyl nicotinate in ibuprofen. FIG. 1 indicates the phases (solid or liquid) present at various temperatures and compositions of the mixture. Thus, it can be seen that the two pharmacologically active agents form a liquid eutectic mixture at compositions between 20–68% (w/w) of ibuprofen in methyl nicotinate, at a temperature of 200° C. The eutectic point occurs at a temperature of −20° C. for a composition of 50% (w/w) ibuprofen in methyl nicotinate.

EXAMPLE B
Oxybutynin-Chlorbutol Eutectic Mixture

Figure 2:
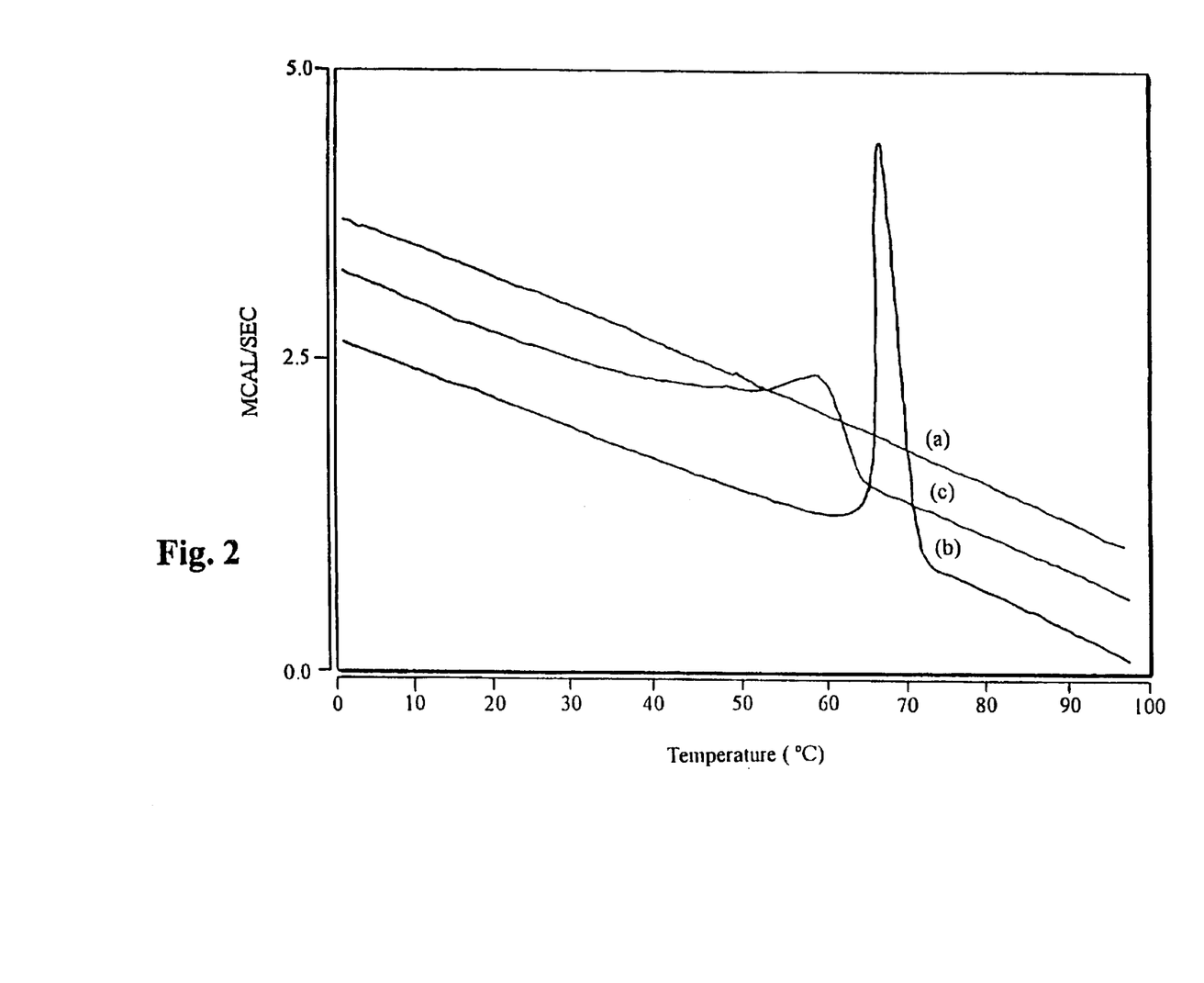

Eutectic mixtures of Example B were prepared at 10% (by weight) composition intervals of the components. The mixtures were heated, allowed to cool to 20° C. and maintained at this temperature for 24 hours. The samples were then analysed by differential scanning calorimetry (DSC) between −5 and +80° C. in order to determine the composition range at which the mixture was in the oil (liquid) phase. Trace (a) of FIG. 2 shows the resulting DSC trace for a 61:39 oxybutynin:chlorbutol (by weight) mixture, in which the lack of an endothermic peak on the trace (an endothermic peak being caused by melting of a solid component) indicates that the eutectic mixture was in the liquid (oil) form throughout the temperature range employed. By contrast, trace (b) of FIG. 2 shows the melting endotherm for pure (solid) chlorbutol (100%) and trace (c) of FIG. 2 shows the depressed chlorbutol melting endotherm for a 15:85 (by weight) mixture of oxybutynin and chlorbutol. The eutectic liquid composition range at 20° C. for Example B was determined as from 40–90% (by weight) oxybutynin.

EXAMPLES C–I

The following Examples C–I of eutectic mixtures useful in the invention were prepared as for Example B and differential scanning calorimetry similarly used to determine the liquid composition range at 20° C. The results are summarised in Table 1.

TABLE 1

Examples of Eutectic Mixtures Useful in the Invention

| Example | Eutectic Mixture | Liquid Composition Range (20° C.) By Weight |
|---|---|---|
| C | Triclosan/Oxybutynin | 10–90% Oxybutynin |
| D | Methyl Cinnamate/Oxybutynin | 40–90% Oxybutynin |
| E | Chlorbutol/Testosterone Enanthate | 40–90% Testosterone Enanthate |
| F | Methyl Nicotinate/Ketoprofen | 40–80% Ketoprofen |
| G | Triclosan/Econazole | 10–90% Econazole |
| H | Sulfiram/Levamisole | 20–70% Levamisole |
| I | Promethazine/Triclosan | 10–80% Triclosan |

In vitro Determination of Penetration Characteristics through a Model Hydrophobic Membrane: General Methodology The penetration characteristics of the actives X and Y from the eutectic compositions of the invention; from comparative simple physical mix systems of X and Y; and from simple non-eutectic systems of X or Y were determined using a model hydrophobic barrier membrane, polydimethylsiloxane sheeting (Silescol™, thickness 0.0625) mm using a Franz finite dose diffusion apparatus, following the Franz method (Franz, T. J., Current Problems in Dermatology, 7, pp58–68 (1978)).

The cell contained 12 ml of phosphate buffered saline, pH 7.4, as the receiving fluid and 1 g of the test composition was applied evenly across the surface of the barrier membrane at the start of the experiment. The receiving fluid in the reservoir was completely replaced with fresh fluid at five minute intervals from the start of the experiment, thus ensuring sink conditions throughout, with the concentration of the active pharmacological agent in each five minute sample being determined by reverse-phase high performance liquid chromatography.

EXAMPLE 1
Ibuprofen-Methyl Nicotinate Eutectic Composition

| | |
|---|---|
| Ibuprofen | 5.00 g |
| Methyl nicotinate | 5.00 g |
| Hydroxyethylcellulose (Natrosol ™ 250 HHX) | 3.00 g |
| Nipastat ™ sodium | 0.20 g |
| Citric acid monohydrate | 1.03 g |
| Disodium phosphate dodecahydrate | 3.65 g |
| Tween 80 | 0.50 g |
| Water | 81.62 g |

A topical composition in the form of an emulsified gel preparation suitable for treating musculo-skeletal disorders is prepared by using a binary eutectic mixture of ibuprofen, an anti-inflammatory analgesic agent, and methyl nicotinate, a rubefacient.

Formulation A is prepared by adding, to the required weight of water in vessel 1, sequentially and with constant stirring, the required weights of citric acid monohydrate, disodium phosphate dodecahydrate and Nipastat™ sodium. In vessel 2, the required weights of ibuprofen and methyl nicotinate are mixed together until the mixture liquefies, and the required weight of Tween 80 is then added with stirring. The contents of vessel 1 are then added to the contents of vessel 2, slowly and with stirring. Finally, the required weight of hydroxyethylcellulose is added slowly and with constant stirring. Formulation A contains a eutectic mixture of the pharmacologically active agents as the internal or discontinuous phase in a gelled emulsion.

Formulation B is identical with Formulation A, except that the emulsifying agent—Tween 80—is omitted. In contrast to Formulation A, Formulation B is merely a physical mixture of the two pharmacologically active agents, in a non-emulsified gel carrier, the eutectic mixture not being maintained, upon dilution in the aqueous phase, in the absence of a stabilizing emulsifier. The function of Formulation B is to compensate for possible competition for fractional area of the barrier membrane available for each of the simultaneously penetrating drugs.

Figure 3A:
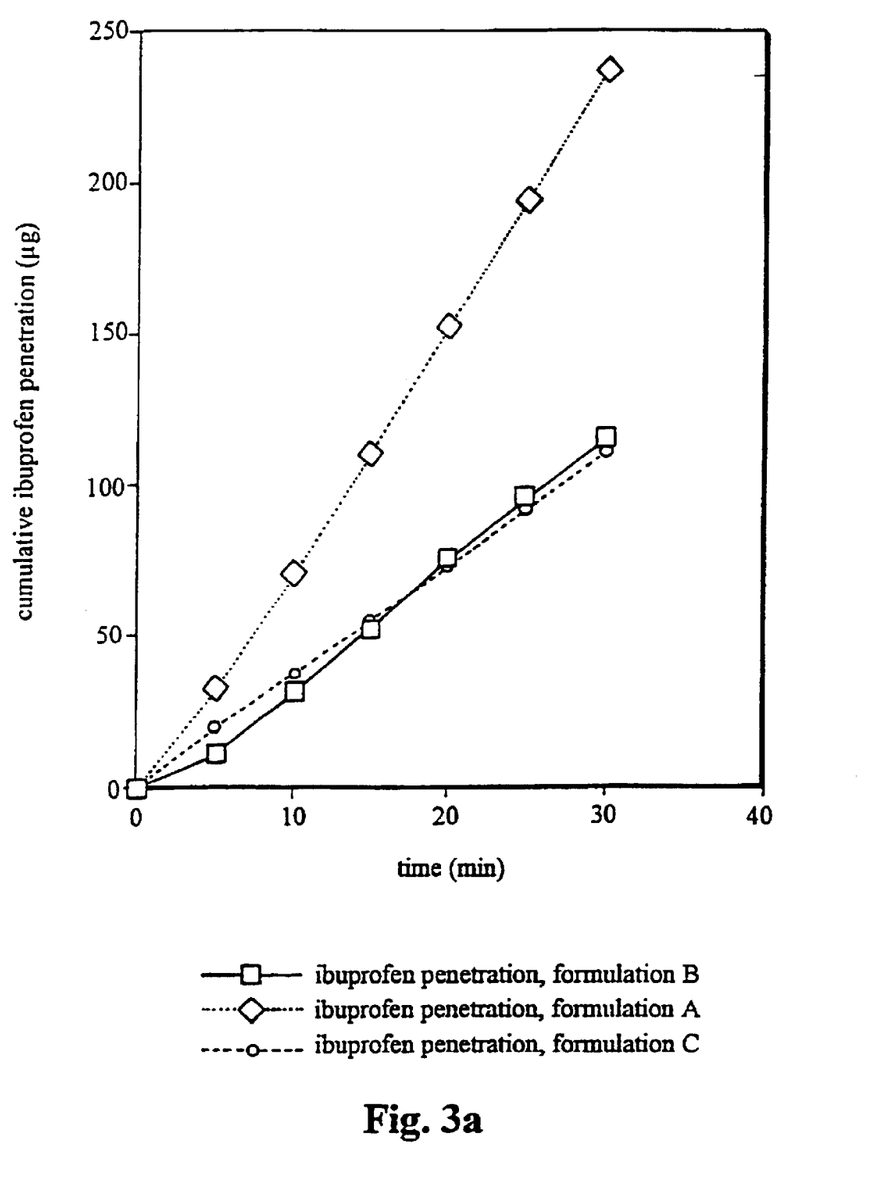
Figure 3B:
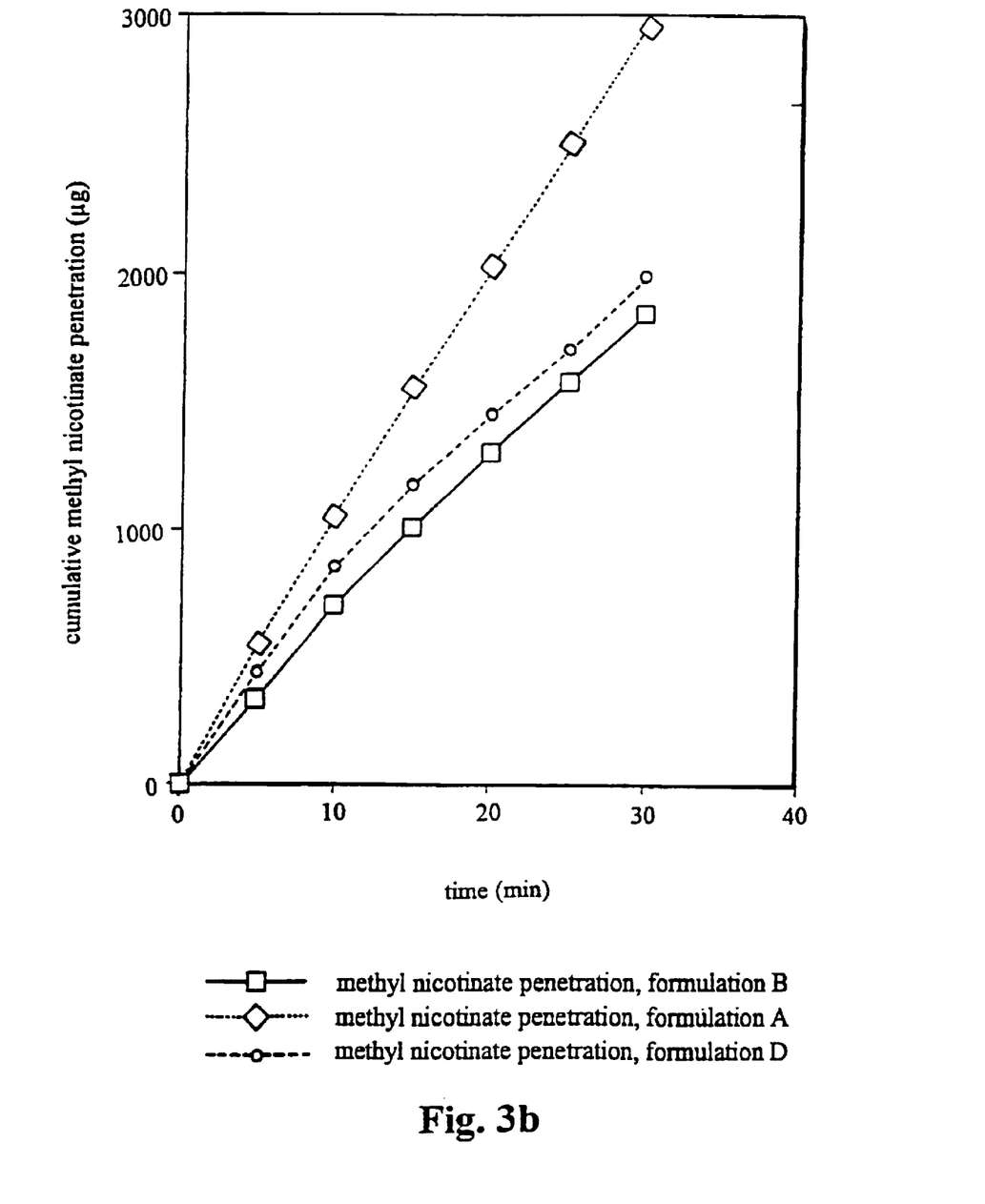

Formulation C is identical with Formulation A, except that methyl nicotinate is omitted and Formulation D is identical to Formulation A except that ibuprofen is omitted. The function of Formulations C and D is to eliminate any possible direct effect of the emulsifier (Tween 80) on the rate of penetration of the pharmacologically active agents. FIGS. 3a and 3b express the respective results obtained as the cumulative amount of each pharmacological agent penetrating the membrane over a 30 minute period for Formulations A–D.

When the penetration rates across the barrier membrane of the two pharmacologically active agents are compared as between Formulations A and B, it is readily apparent from FIGS. 3a and 3b that significantly greater rates of penetration for both agents are achieved with the topical composition of the present invention. Indeed, the rate of penetration of ibuprofen observed with the eutectic Formulation A is almost double that of the non-eutectic Formulation B.

Formulations C and D gave rates of penetration for ibuprofen and methyl nicotinate, respectively, almost identical to those obtained with Formulation B (see FIGS. 3a and 3b, respectively). This confirms that the enhanced penetration observed for Formulation A is not due to the presence of an emulsifier and points, instead, to the presence of a eutectic mixture in Formulation A as the cause of the enhanced penetration observed.

General Method of Manufacture for Eutectic Compositions in Examples 2–6

The following general method was used to manufacture topical compositions of the invention in order to determine their in vitro permeation characteristics through a model hydrophobic membrane. The two pharmacologically active components of the topical compositions are designated X and Y in the general method of manufacture. It will be realised by those skilled in the art that a number of alternative methods and excipients may be used with equal facility to manufacture the examples of the invention and that the disclosure of such examples in no way limits the scope of the invention.

A mixture of sorbitan stearate and sucrose cocoate, a commercially available emulsifier—Arlatone™ 2121 (4.0 g), was added to distilled water (83.9 g) at 80° C. with stirring. An emulsion stabiliser, xanthan gum (0.1 g), commercially available as Keltrol™, was added to the solution. In a separate heated vessel, a 50:50 mixture (by weight) of the eutectic-forming active agents X and Y were melted together to form a transparent, homogeneous oil. The eutectic mixture (10.0 g) was added to the heated aqueous phase with intensive stirring and the system homogenised through a Silversun homogeniser for two minutes to form an oil-in-water emulsion, the oil phase comprising the eutectic mixture. The emulsion was then allowed to cool to room temperature. Finally, hydroxyethylcellulose (2.0 g), commercially available as Natrosol™ (Grade HHX), was added as a viscosity builder and the resulting higher viscosity product homogenised for a further 2 minutes before being dispensed in 30 g lacquered ointment tubes. The viscosity builder is dispersed in the continuous aqueous phase and not in the oil phase. No solid drug particles are evident on visual or light microscopic examination.

Preparation of Non-Eutectic Comparative Compositions

In order to demonstrate the mutually enhanced penetration characteristics of the active agents X and Y in eutectic compositions of the invention over comparative non-eutectic compositions of the same active components, comparative compositions were prepared containing non-eutectic physical mixtures of X and Y, each in the solid state, as follows. Natrosol HHX (2.0 g) was added as a viscosity builder to distilled water (88.0 g) at ambient temperature with intensive stirring and the resulting gel homogenised for 2 minutes as described hereinbefore. The viscosity builder, by increasing the viscosity, serves to prevent intimate contact between the eutectic-forming components. Active component X (5.0 g) and active component Y (5.0 g) were added separately and sequentially to the gel and the whole homogenised for a further 2 minutes before being dispensed in 30 g lacquered ointment tubes. The viscosity on the Brookfield scale of this non-eutectic system was within ±2% of that of the equivalent eutectic composition. Solid drug particles are evident on visual and light microscopic examination.

EXAMPLE 2
Ibuprofen-Methyl Nicotinate Eutectic Composition

Figure 4A:
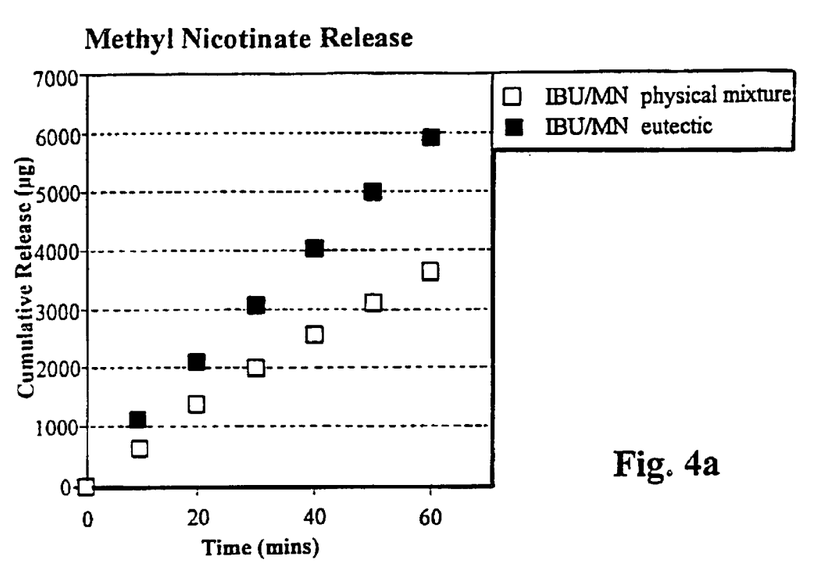
Figure 4B:
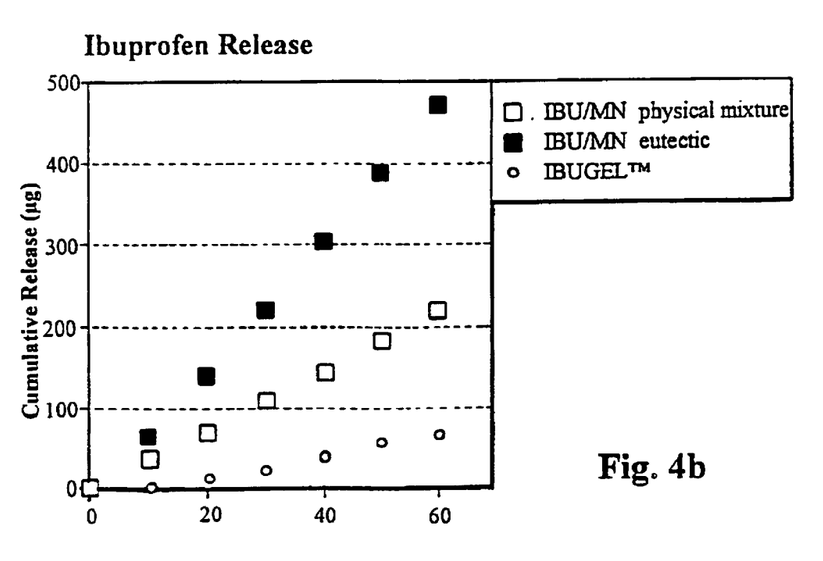

A topical eutectic composition in the form of an emulsified gel preparation suitable for treating musculo-skeletal disorders was prepared by the general method described hereinbefore using a binary eutectic mixture of ibuprofen (X), an anti-inflammatory analgesic agent, and methyl nicotinate (Y), a rubefacient. A non-eutectic comparative composition was also prepared by the comparative method described hereinbefore. The penetration of methyl nicotinate and ibuprofen through the model barrier membrane was determined for both eutectic and non-eutectic systems. The results are presented in FIGS. 4a and 4b, respectively, whereupon it is readily apparent that enhanced delivery is achieved for both methyl nicotinate and ibuprofen from the eutectic composition. FIG. 4b shows, in addition, the cumulative ibuprofen release through the same model barrier membrane from Ibugel (Trade Mark), a commercially available non-eutectic gel formulation. It is clear that ibuprofen delivery from Ibugel (Trade Mark) is markedly less than that observed for the eutectic composition of the present invention and, indeed, even less than that observed for the comparative non-eutectic composition.

EXAMPLE 3
Promethazine-Benzocaine Eutectic Composition

Figure 5A:
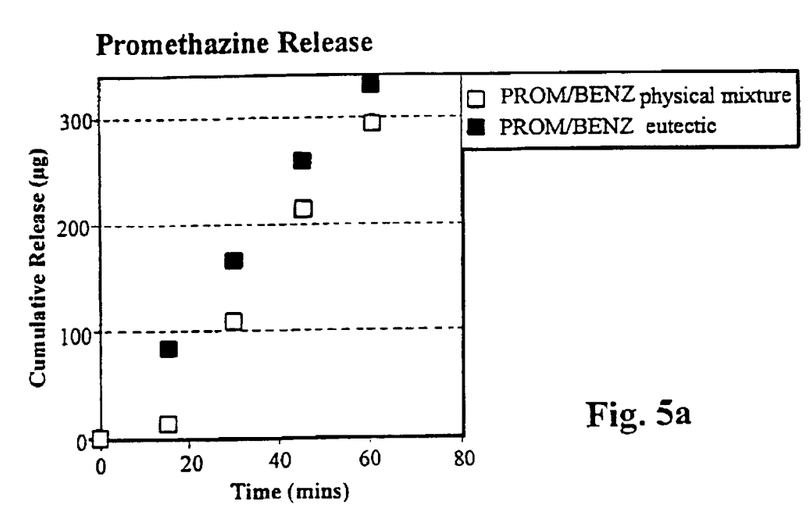
Figure 5B:
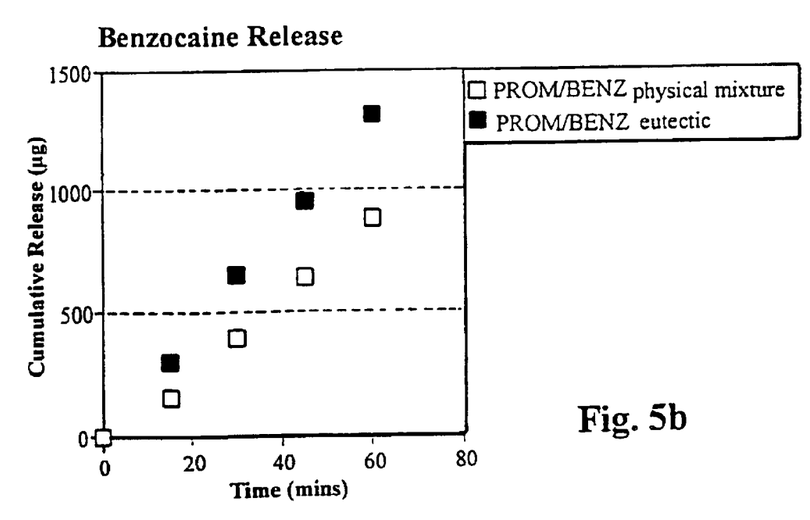

A topical eutectic composition in the form of an emulsified gel preparation suitable for treating allergic and inflammatory pruritic skin conditions was prepared by the general method described hereinbefore using a binary eutectic mixture of promethazine (X), an anti-pruritic agent, and benzocaine (Y), a rubefacient. A non-eutectic comparative formulation was also prepared by the comparative method described hereinbefore. The penetration of promethazine and benzocaine through the model barrier membrane was determined for both eutectic and non-eutectic systems. The results are presented in FIGS. 5a and 5b, whereupon it is readily apparent that enhanced delivery is achieved for both promethazine and benzocaine from the eutectic composition.

EXAMPLE 4
Levamisole-Sulfiram Eutectic Composition

Figure 6A:
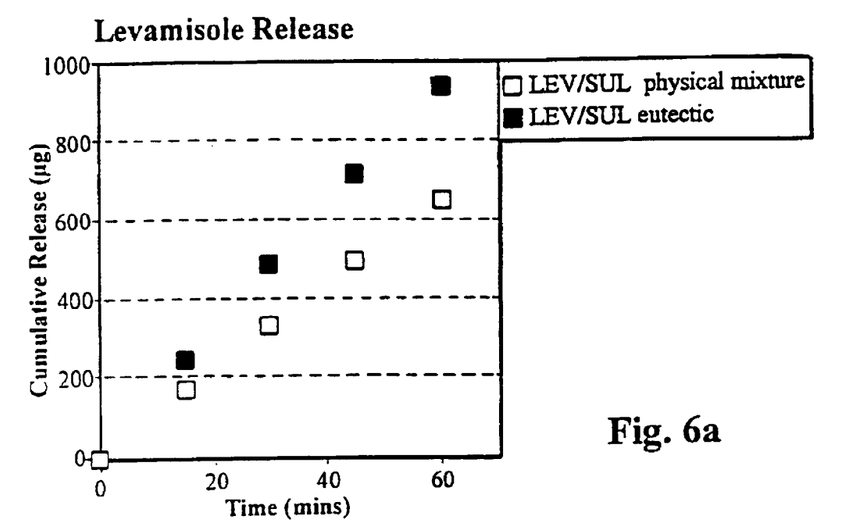
Figure 6B:
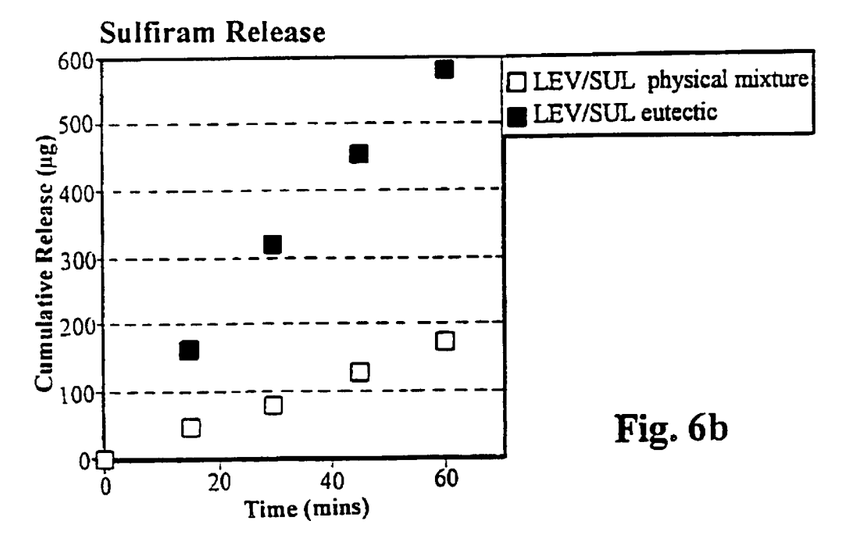

A topical eutectic composition in the form of an emulsified gel preparation suitable for treating ectoparasitic and anthelminthic infestations in non-human animals was prepared by the general method described hereinbefore using a binary eutectic mixture of levamisole (X), an anthelminthic, and sulfiram (Y), an ectoparasitic agent. A non-eutectic comparative formulation was also prepared by the comparative method described hereinbefore. The penetration of levamisole and sulfiram through the model barrier membrane was determined for both eutectic and non-eutectic systems. The results are presented in FIGS. 6a and 6b, whereupon it is readily apparent that enhanced delivery is achieved for both levamisole and sulfiram from the eutectic composition.

EXAMPLE 5
Oxybutynin-Chlorbutol Eutectic Composition

Figure 7A:
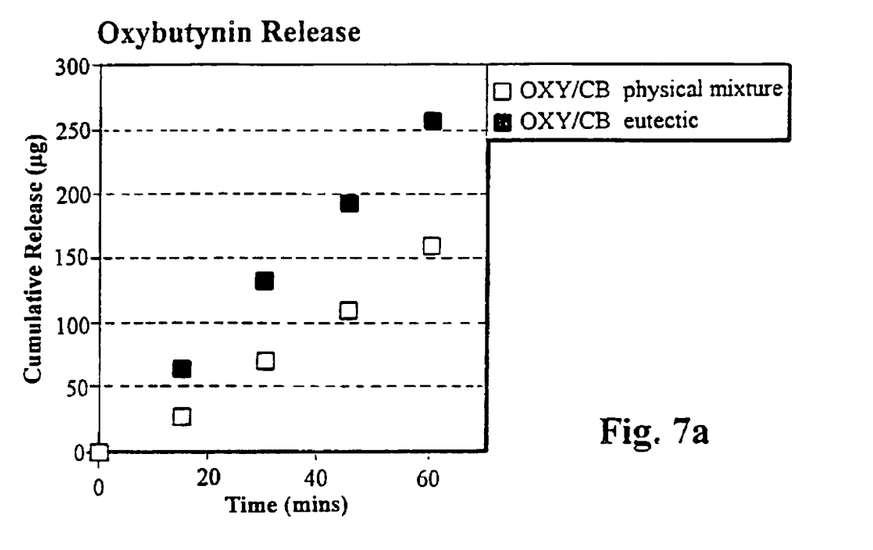
Figure 7B:
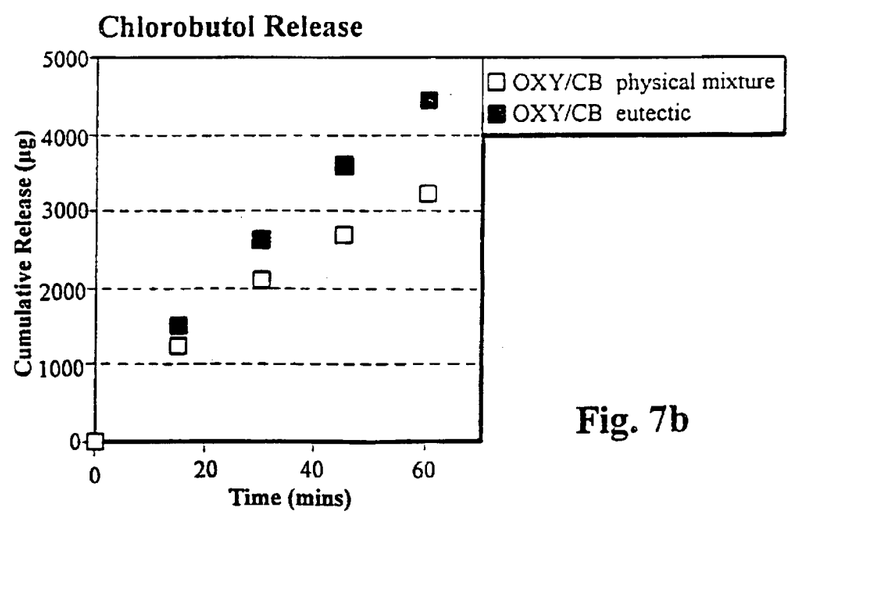

A topical eutectic composition in the form of an emulsified gel preparation suitable for treating spasmodic conditions such as urinary incontinence by transdermal delivery was prepared by the general method described hereinbefore using a binary eutectic mixture of oxybutynin (X), an anti-spasmodic agent, and chlorbutol (Y), an antimicrobial agent/preservative. A non-eutectic comparative formulation was also prepared by the comparative method described hereinbefore. The penetration of oxybutynin and chlorbutol through the model barrier membrane was determined for both eutectic and non-eutectic systems. The results are presented in FIGS. 7a and 7b, whereupon it is readily apparent that enhanced delivery is achieved for both oxybutynin and chlorbutol from the eutectic composition.

EXAMPLE 6
Ketoprofen-Benzocaine Eutectic Composition

Figure 8A:
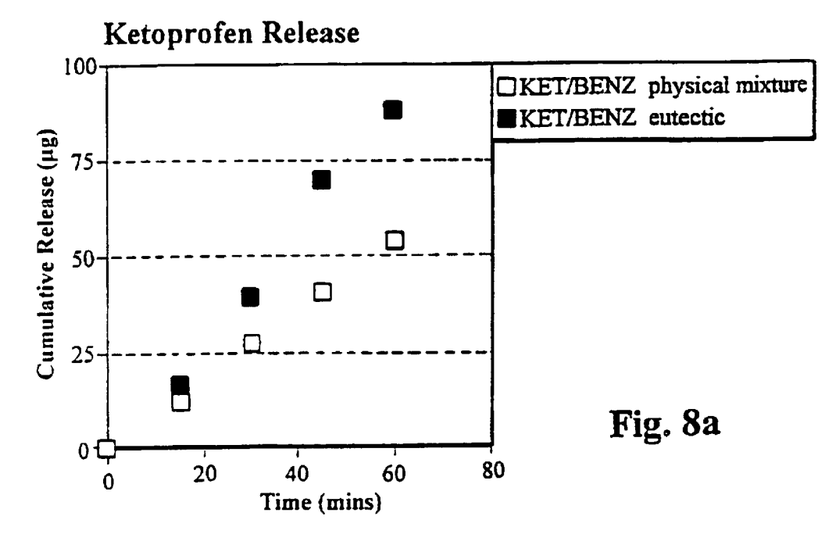
Figure 8B:
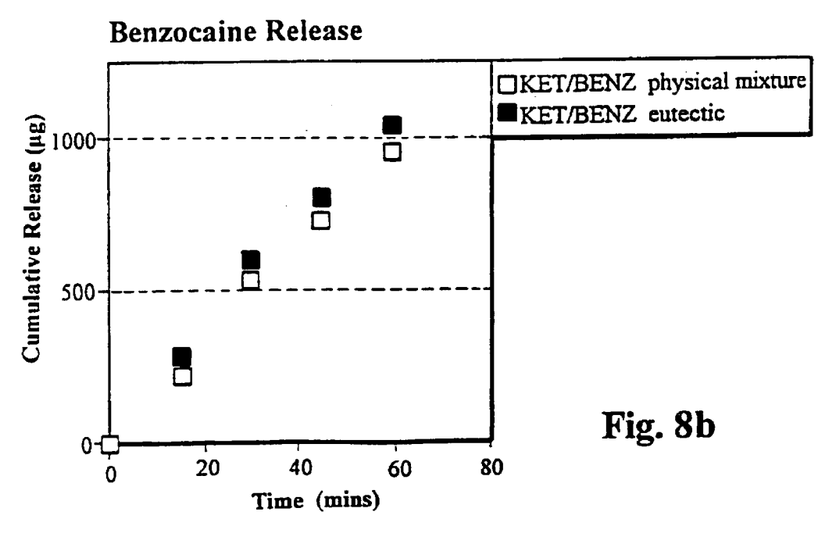

A topical eutectic composition in the form of an emulsified gel preparation suitable for treating soft tissue injuries was prepared by the general method described hereinbefore using a binary eutectic mixture of ketoprofen (X), an anti-inflammatory agent, and benzocaine (Y), a local anaesthetic. A non-eutectic comparative formulation was also prepared by the comparative method described hereinbefore. The penetration of ketoprofen and benzocaine through the model barrier membrane was determined for both eutectic and non-eutectic systems. The results are presented in FIGS. 8a and 8b, whereupon it is readily apparent that enhanced delivery is achieved for both ketoprofen and benzocaine from the eutectic composition.

What is claimed is:

1. A topical composition for mutual enhancement of transdermal permeation of at least a first and a second pharmaceutically acceptable components which are both pharmacologically active agents, the composition comprising an emulsion of at least one discontinuous phase in a continuous phase, the at least one discontinuous phase comprising a eutectic mixture of at least first and second pharmacologically active agents and the continuous phase comprising a pharmaceutically acceptable carrier, the eutectic mixture having a melting point below 40° C.; and at least one compatible emulsifying agent, wherein the first pharmacologically active agent is selected from the group consisting of chlorocresol, chlorbutanol, methyl nicotinate, triprolidine, promethazine, trimeprazine, sulfiram, oxybutynin, testosterone enanthate, and choline salicylate, wherein the second pharmacologically active agent is selected from the group consisting of chlorocresol, trimeprazine, choline salicylate, methyl nicotinate, ibuprofen, ketoprofen, fenoprofen, flurbiprofen etodolac, fentanyl, econzole, ketoconazole, mupirocin, chlorbutanol, clindamycin, iodine, oxybutynin, tetramisole, triprolidine, promethazine, and propranolol, in which the at least two pharmacologically active agents are structurally and/or pharmacologically diverse, wherein when the first pharmacologically active agent is a local anesthetic, the second pharmacologically active agent is not a local anaesthetic, wherein when the second pharmacologically active agent is a local anesthetic, the first pharmacologically active agent is not a local anesthetic, and wherein the first and the second pharmacologically active agents are each a prophylactic or a therapeutic agent.

2. The topical composition according to claim 1, in which the first pharmacologically active agent has a melting point between 35 and 75° C., and the second pharmacologically active agent has a melting point between −40° C. and 150° C.

3. The topical composition according to claim 1, in which the topical composition additionally includes, in the eutectic mixture, a third pharmaceutically acceptable component.

4. The topical composition according to claim 3, in which the third pharmaceutically acceptable component has a melting point between 40 and 150° C.

5. The topical composition according to claim 3 or 4, in which the third component is a third pharmacologically active agent.

6. The topical composition according to claim 3, in which the topical composition additionally includes, in the eutectic mixture, a fourth pharmaceutically acceptable component.

7. The topical composition according to claim 6, in which the fourth pharmaceutically acceptable component has a melting point between 40 and 150° C.

8. The topical composition according to claim 6 or 7, in which the fourth component comprises a fourth pharmacologically active agent.

9. The topical composition according to claim 1, in which said at least one discontinuous phase consists essentially of the eutectic mixture.

10. The topical composition according to claim 8, in which the third and fourth pharmacologically active agents are each selected from the group consisting of non-steroid anti-inflammatory agents, narcotic analgesics, anti-fungal agents, antibacterial agents, anticholinergics, antihypertensives, antihistaminics, and anthelmintics.

11. The topical composition according to claim 3 or 4, in which the third pharmaceutically acceptable component is lauric acid, stearyl alcohol, menthol, thymol, cinnamic acid, or an ester thereof.

12. The topical composition according to claim 1, in which the pharmaceutically acceptable carrier is substantially hydrophilic.

13. The topical composition according to claim 1, in which the pharmaceutically acceptable carrier contains at least one gelling or suspension agent.

14. The topical composition according to claim 13, in which the gelling or suspension agent is selected from the group consisting of carbomers, naturally-occurring synthetic or semi-synthetic gums, co-polymers formed between maleic anhydride and methyl vinyl ether, colloidal silica and methacrylates, and a mixture thereof.

15. The topical composition according to claim 1, in which the topical composition is in the form of a gel, lotion, suspension, cream, aerosol spray, is deposited on a transdermal patch, or medicated dressing or is incorporated within soft gelatin capsule.

16. The topical composition according to claim 1, in which the emulsifying agent is selected from the group consisting of non-ionic, cationic and anionic surfactants.

17. The topical composition according to claim 16, in which the emulsifying agent is a non-ionic surfactant.

18. A method for mutual enhancement of dermal permeation of at least a first and a second pharmaceutically acceptable components which are both pharmacologically active agents, the method comprising applying a topical composition to a human in need thereof for mutual enhancement of transdermal permeation of at least the first and second pharmacologically active agents, the composition comprising an emulsion of at least one discontinuous phase in a continuous phase, the at least one discontinuous phase comprising a eutectic mixture of at least first and second pharmacologically active agents and the continuous phase comprising a pharmaceutically acceptable carrier, the eutectic mixture having a melting point below 40° C.; and at least one compatible emulsifying agent, wherein the first pharmacologically active agent is selected from the group consisting of triclosan, chlorocresol, chlorbutanol, methyl nicotinate, triprolidine, promethazine, trimeprazine, sulfiram, oxybutynin, testosterone enanthate, and choline salicylate, wherein the second pharmacologically active agent is selected from the group consisting of triclosan, chlorocresol, capsaicin, trimeprazine, choline salicylate, methyl nicotinate, ibuprofen, ketoprofen, fenoprofen, flurbiprofen, etodolac, fentanyl, econzole, ketoconazole, mupirocin, chlorbutanol, clindamycin, iodine, oxybutynin, tetramisole, triprolidine, promethazine, and propranolol, in which the at least two pharmacologically active agents are structurally and/or pharmacologically diverse, and wherein when the first pharmacologically active agent is a local anesthetic, the second pharmacologically agent is not a local anesthetic, wherein when the second pharmacologically active agent is a local anesthetic, the first pharmacologically active agent is not a local anesthetic, wherein the topical application to a human in need thereof is to a body surface of the human.

19. The topical composition according to claim 2, wherein the first pharmacologically active agent has a melting point between 40 and 50° C., and the second pharmacologically active agent has a melting point between −5 and 90° C.

20. The topical composition according to claim 4, wherein the third pharmaceutically acceptable component has a melting point between 40 and 75° C.

21. The topical composition according to claim 7, wherein the fourth pharmaceutically acceptable component has a melting point between 40 and 75° C.

22. The topical composition according to claim 10, wherein the third and fourth pharmaceutically active agents are each selected from the group consisting of triclosan, chlorocresol, capsaicin, trimeprazine, choline salicylate, methyl nicotinate, ibuprofen, ketoprofen, fenoprofen, flurbiprofen, etodolac, fentanyl, econazole, ketoconazole, mupirocin, chlorbutanol, clindamycin, iodine, oxybutynin, propranolol, triprolidine, promethazine, and tetramisole.

23. The topical composition according to claim 14, wherein the gelling or suspension agent is selected from the group consisting of xanthan gum, acacia, tragacanth, and a mixture thereof.

24. The topical composition according to claim 9, in which said at least one discontinuous phase is the eutectic mixture.

25. The topical composition according to claim 12, in which the pharmaceutically acceptable carrier essentially consists of water as the continuous phase.

26. The method according to claim 18, in which said at least one discontinuous phase consists essentially of the eutectic mixture.

27. The method according to claim 26, in which said at least one discontinuous phase is the eutectic mixture.

28. The method according to claim 18, in which the pharmaceutically acceptable carrier is substantially hydrophilic.

29. The method according to claim 28, in which the pharmaceutically acceptable carrier essentially consists of water as the continuous phase.

* * * * *